(12) United States Patent
Glenn et al.

(10) Patent No.: US 8,512,726 B1
(45) Date of Patent: Aug. 20, 2013

(54) MOLECULAR GEL-BASED CONTROL RELEASE DEVICES FOR PHEROMONES

(75) Inventors: Gregory M. Glenn, American Canyon, CA (US); George John, New York, NY (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/272,207

(22) Filed: Oct. 12, 2011

Related U.S. Application Data

(60) Provisional application No. 61/392,433, filed on Oct. 12, 2010.

(51) Int. Cl.
*A01N 25/08* (2006.01)
*A61L 9/04* (2006.01)

(52) U.S. Cl.
USPC ................................ 424/409; 239/57; 239/60

(58) Field of Classification Search
USPC .............................. 424/409, 410; 239/55, 60
See application file for complete search history.

(56) References Cited

U.S. PATENT DOCUMENTS

| 4,809,912 | A | * | 3/1989 | Santini ........................ 239/60 |
| 5,316,148 | A | * | 5/1994 | Neumann et al. .......... 206/484.1 |
| 7,994,138 | B2 | * | 8/2011 | Awada et al. .................. 514/23 |
| 2007/0148202 | A1 | * | 6/2007 | Primo Yufera et al. ....... 424/410 |

OTHER PUBLICATIONS

G. M. Glenn; et al., "Permeability of Starch Gel Matrices and Select Films to Solvent Vapors", Journal of Agricultural and Food Chemistry, 2006, 54 (9), pp. 3297-3304, published Apr. 20006 by the Royal Soc. of Chem.*

* cited by examiner

*Primary Examiner* — Janet Epps-Smith
*Assistant Examiner* — Yanzhi Zhang
(74) *Attorney, Agent, or Firm* — Elizabeth R. Sampson; Lesley Shaw; John Fado (57) ABSTRACT

The present invention relates to aryl glycolipid gels as control release devices and uses thereof in agriculture. In an exemplary embodiment, mannitol dioctanoate (M8) is used to prepare controlled release devices for pheromones.

14 Claims, 9 Drawing Sheets

MOLECULAR GEL-BASED CONTROL RELEASE DEVICES FOR PHEROMONES

CROSS REFERENCE TO RELATED APPLICATIONS

This application claims priority to U.S. Provisional Patent Application Ser. No. 61/392,433, filed Oct. 12, 2010 which is incorporated herein by reference in its entirety.

BACKGROUND OF THE INVENTION

Pheromones are naturally obtained volatile semiochemicals and are considered as effective biopesticides under the integrated pest management concept.1,2 They induce confusion and impair the sexual communication of pests. The high species-specificity of pheromones further enables pest control without weakening beneficial organisms.

Numerous reservoir-type controlled release devices (CRDs) have been developed for pest control which are designed to overcome the high volatility of pheromones and achieve a sustained release over a period of several weeks. However, current devices are typically polymeric, involve multi-step preparation protocols, exhibit low pheromone-holding capacities and are not readily biodegradable. Moreover, most of the devices leak if they are broken or compressed. Thus, for agricultural applications, particularly for applications in organic agriculture, such devices are clearly inferior.

Therefore, a need exists in the art for controlled release devices (CRDs) that is effective for releasing pheromones in a controlled manner, to provide a consistent and reliable dose pheromones, but which does not generate significant amounts of waste that is not easily biodegraded or disposed of. Amongst other virtuous attributes, such a controlled release device would be both convenient and environmentally sound. Fortunately, as will be clear from the following disclosure, the present invention provides for these and other needs.

SUMMARY OF THE INVENTION

In one aspect, the present invention provides a controlled release device (CRD) comprising: a solid gel of a pheromone, and an impermeable membrane at least partially surrounding the solid gel of pheromone, wherein the solid gel comprises, in addition to the pheromone, an amphiphilic ester.

In another aspect, the present invention provides a controlled release device (CRD) comprising a solid gel of 2-heptanone, and an impermeable film at least partially surrounding the solid gel of 2-heptanone, wherein the solid gel of 2-heptanone comprises mannitol dioctanoate (M8) at a concentration that is in a range of between about 5% weight/weight (w/w) to about 7% w/w.

In another aspect, the present invention provides a method for controlling Varroa mites in honey bee hives, the method comprising placing a controlled release device (CRD) into a honey bee hive, wherein the controlled release device comprises a solid gel of 2-heptanone, and an impermeable film at least partially surrounding the solid gel of 2-heptanone wherein the solid gel of 2-heptanone comprises mannitol dioctanoate (M8) at a concentration that is in a range of between about 5% weight/weight (w/w) to about 7% w/w.

Other features, objects and advantages of the invention will be apparent from the detailed description which follows.

DETAILED DESCRIPTION OF THE INVENTION

Definitions

Unless defined otherwise, all technical and scientific terms used herein generally have the same meaning as commonly understood by one of ordinary skill in the art to which this invention belongs.

The term "alcohol" as used herein, refers to a chemical compound of the formula R—OH, wherein R is an alkyl, aryl, substituted alkyl or substituted aryl group. A "lower alcohol" refers to an alkane, alkene, or alkyne of one to six carbon atoms substituted with at least one hydroxyl group.

The term "ketone" as used herein, refers to a chemical compound of the formula R—(CO)—R', wherein R is an alkyl, aryl, substituted alkyl or substituted aryl group and wherein R' is an alkyl, aryl, substituted alkyl or substituted aryl group that is the same or different than R.

The term "alkyl," is used in the conventional sense. Thus, the term "alkyl," by itself or as part of another substituent means, unless otherwise stated, a straight or branched chain, or cyclic hydrocarbon radical, or combination thereof, which may be fully saturated, mono- or polyunsaturated and can include di- and multivalent radicals, having the number of carbon atoms designated (e.g., $C_1$-$C_{10}$ meaning one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Exemplary unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," is used in the conventional sense. Thus, the term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Exemplary "heteroalkyl" groups include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—CH-3, —$CH_2$—$CH_2$,—S(O)—$CH_3$,—$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)2R'— represents both —C(O)2R'— and —R'C(O)$_2$—.

Each of the above terms (e.g., "alkyl," and "heteroalkyl,") is meant to include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from one to four heteroatoms selected from the group consisting of N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl and 8-quinolyl. Substituents for each of the above noted aryl and heteroaryl ring systems are selected from the group consisting of the group of acceptable substituents described below.

Substituents for the aryl and heteroaryl groups are varied and are selected from the group consisting of: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$ $C_4$)alkoxy, and perfluoro($C_1$ $C_4$)alkyl, in a number ranging from zero to the total number of open valences on the aromatic ring system; and where R', R" and R'" are independently selected from the group consisting of hydrogen, ($C_1$ $C_8$)alkyl and heteroalkyl, unsubstituted aryl and heteroaryl, (unsubstituted aryl)-($C_1$ $C_4$)alkyl, and (unsubstituted aryl)oxy-($C_1$ $C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH2) r-B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from the group consisting of hydrogen or unsubstituted (C$_1$ C$_6$)alkyl.

As used herein, the term "heteroatom" is meant to include oxygen (O), nitrogen (N), sulfur (S) and silicon (Si).

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical, unless otherwise indicated.

The term "water-miscible" as used herein refers to substances that have at least some degree of miscibility in water. For example, a water miscible liquid or water miscible solvent is typically at least partially miscible with water. In an exemplary embodiment, a water miscible solvent has a solubility of at least about 50 parts by weight per 100 parts by weight of water. In other exemplary embodiments, a water miscible liquid or water miscible solvent has a solubility of at least about 100 parts by weight per 100 parts by weight of water. In other exemplary embodiments a water miscible solvent is miscible with water in all proportions. Thus, a "water-miscible solvent" is capable of being mixed with, and forming a continuous single phase with water. Exemplary water miscible solvents include, but are not limited to water, ethanol, isopropanol, acetic acid, dimethylsulfoxide, acetone, propylene glycol, etc.

The term "biodegradable" as used herein refers to a composition or substance that decays and becomes absorbed by the environment. A biodegradable substance is capable of decaying through the action of living organisms typically, through the action of living organisms such as bacteria and fungi. Biodegradation of biodegradable substances such as food and sewage, typically leads to compaction and liquefaction, and to the release of nutrients that are then recycled by the ecosystem.

As used herein, the term "control" or "controlling" as in e.g., the phrase: the "control" of Varroa mites, or "controlling" Varroa mites, or as in the phrase: "controlling" agricultural pests, refers to any means for preventing infection or infestation, reducing the population of already infected areas or organisms, or elimination of the population of pests or mites or other species whose "control" is desired. Indeed, "controlling" as used herein refers to any indica of success in prevention, elimination, reduction or amelioration of a pest population or pest problem.

The term "controlled release" or "control-release" or any other grammatically equivalent expression, refers to means for adjusting the release rate e.g., vapor transmission rate, of a volatile chemical or substance by comparison to the release rate that would be achieved without any "controlled release" measures. Indeed, "controlled release" as used herein refers to any indica of success in altering the release rate of a volatile chemical or substance. Typically, without "controlled release" the vapor transmission rate of a volatile substance is faster than the vapor transmission rate when "controlled release" is in effect. Thus, in some exemplary embodiments, "control-release" is synonymous with "slow release" since in some exemplary embodiments, "control-release" refers to slowing of the vapor transmission rate.

The term "bee colony" or "honeybee colony" as used herein, refers to a social unit of bees, e.g., honeybees comprising a colony. The social unit can be of any system organization utilized by bees which has the purpose of facilitating survival of the group or colony. Typically, a "bee colony" consists of several thousand bees that cooperate in nest building, food collection, and brood rearing. Each member of a "bee colony" has a definite task to perform, and it takes the combined efforts of the entire colony to survive and reproduce. A colony typically comprises a single queen, thousands of workers, and hundreds of drones during late spring and summer. Typically, the population of a "bee colony" peaks from late spring to summer and reaches a low point in winter. The social structure of the colony is maintained by the queen and workers and depends on an effective system of communication. Domesticated honeybees are cultivated in "beehives" or "honeybee hives". Thus the term "beehive" or "honeybee hive" refers to a structure that functions as a habitation for a colony of bees, e.g., a colony of honeybees.

The term "behavior modifying compound" as used herein refers to any substance or compound which influences the behavior or development of an organism e.g, stimulates a mating dance, and/or helps the organism find food, escape enemies and/or find a mate. Such substances can be naturally occurring or synthetically made. For example, "behavior-modifying compounds" include, but are not limited to e.g., semiochemicals such as e.g., pheromones, allomones, and kairomones.

The term "pheromone" as used herein, refers to a substance or mixture of substances which are secreted and released by an organism for detection and response by another organism of the same species. Pheromones mediate a variety of interactions between organisms. Thus, pheromones are typically classified by the interaction that they most strongly influence e.g., alarm, aggregation or sex pheromone.

As is known in the art, "pheromones" belong to the larger class of chemical compounds referred to as semiochemicals. The term "semiochemical" as used herein refers to chemicals that mediate interactions between organisms. Semiochemicals include allelochemicals and pheromones depending on whether the interactions are interspecific or intraspecific, respectively. As used herein the term "allelochemical" refers to chemical substances that induce a response in the receiver of the signal that is either adaptively favorable to the emitter but not the receiver (allomones), or that is favorable to the receiver but not the emitter (kairomones) or is favorable to both emitter and receiver (synomones). Allelochemicals and pheromones are useful e.g, as arrestants, attractants, repellents, deterrents, and/or stimulants.

The term "2-heptanone" or "heptane-2-one" as used herein, refers to a ketone that in its natural state is a component of the honey bee mandibular gland pheromone. 2-heptanone is known in the art (see e.g., U.S. Pat. No. 6,843,985). In honey bees 2-heptanone is a pheromone produced by the mandibular glands of adult worker honey bees, *Apis mellifera* and *Apis cerana* older than 8-10 days (see e.g., Vallet et al., J.

Insect Physiol. 37(11):789-804 (1991); and Sakamoto et al., Journal of Apiculture Research 29(4):199-205 (1990)).

In some exemplary embodiments a solid gel is prepared comprising a pheromone a mixture of pheromones wherein the pheromone is a member selected from the group consisting of 2-heptanone laurel acetate, 1-Octen-3-ol, Z-3-Decenyl Acetate, 6-acetoxy-5-Hexadecanolide, Z-7-Decenyl Acetate, cis-5-Decenyl acetate, e,e-8,10-DODECADIEN-1-YL ACETATE, 8,10-Dodecadien-1-ol, z-5-DODECEN-1-YL ACETATE, e-7-Dodecen-1-yl acetate, E-beta-farnesene, Cyclobutaneethanol, 1-methyl-2-(1-methylethenyl)-, cis-3, 3-Dimethyl-D1,b-cyclohexaneethanol, (Z)-3,3-Dimethyl-D1,acyclohexaneacetaldehyde, cis-6-Heneicosen-11-one, (cis-7,cis-11/cis-7,trans-11)-Hexadecadienyl acetate, and 4-Methyl-5-Nonanone or a combination of one or more said pheromones.

I. Introduction: Aryl Glycolipid Gels

The use of a biobased gelators provides for devices are highly biocompatible and biodegradable. In an exemplary embodiment, molecular gels find applications in the agricultural industry as efficient controlled release devices for pheromones. In sme embodiments, pheromones released by the molecular gels disclosed herein are also biopesticides. Such new devices are readily biodegradable, exhibit high pheromone-loading capacity and deliver the pesticide uniformly at high concentration for a prolonged time.

Molecular gelators (MGs) are low molecular weight amphiphilic molecules that self-assemble through non-covalent forces to form a volume-filling 3-D network. See e.g., R. G. Weiss and P. Terech, Molecular gels. Materials with Self-assembled Fibrillar Networks, Springer, Dordrecht, The Netherlands, 2005; A. R. Hirst, B. Escuder, J. F. Miravet and D. K. Smith, Angew. Chem., Int. Ed., 2008, 47, 8002; F. Zhao, M.-L. Mab and B. Xu, Chem. Soc. Rev., 2009, 38, 883. As is known in the art, within the network, solvent molecules are immobilized by physical interactions such as surface tension, thereby converting the liquid into a coherent gel. An exemplary molecular gelator is mannitol dioctanoate (M8).

As will be disclosed in detail hereinbelow, molecular gels are useful in the agricultural industry as controlled release devices for pheromones, which are potential biopesticides. Such new devices are readily biodegradable, exhibit high pheromone-loading capacity and deliver the pesticide uniformly at high concentration for a prolonged time.

II. Gelling Materials

Sugar alcohol-based amphiphiles having an unprecedented gelation property towards hydrophobic liquids have been developed (see e.g., S. R. Jadhav, P. K. Vemula, R. Kumar, S. R. Raghavan and G. John, Angew. Chem., Int. Ed., 2010, 49, 7695, which is incorporated herein by reference). One of the sugar alcohol based amphiphiles mannitol dioctanoate (M8) was found to be particularly versatile. M8 is a conjugate of biobased and highly biocompatible raw materials; mannitol and fatty acids. Thus, M8 exhibits good biodegradability and minimal carbon footprint.

Gelling materials e.g., mannitol dioctanoate (M8) can be present in any effective concemtration. Typically, a gelling material or molecular gelator e.g., mannitol dioctanoate (M8), is present in a concentration of between about 0.5% to about 10%. In some exemplary embodiments a molecular gelator or a aryl glycolipid e.g., mannitol dioctanoate (M8) is present in a concentration of about 1%, about 1.5%, about 2%, about 3%, about 4%, about 5%, about 6%, about 7%, about 8%, about 9%, about 10%.

Thus, in exemplary embodiments, mannitol dioctanoate (M8), is used to efficiently gel pheromones that are used in organic agriculture e.g., in apiculture.

B. Solidity of Aryl Glycolipid Gels Gel Articles

The solidity and/or rigidity of an aryl glycolipid gel article is readily determined by any method known in the art. For example, in one exemplary embodiment, the solidity of an aryl glycolipid gel measured by methods known in the art (see e.g., Meyer, M. A. and Chawla, K. K. *Mechanical Behavior of Materials* Prentice-Hall, (1999), 680 pp). For example in some exemplary embodiments the solidity of a semi rigid gel is expressed as the linear viscoelastic response measured in an oscillatory test using a Dynamic Mechanical Analyzer (see e.g., Barnes, Howard A., *A Handbook of Elementary Rheology*, Institute of Non-Newtonian Fluid Mechanics, University of Wales, 2000).

In other exemplary embodiments, the solidity of an aryl glycolipid gel is measured by determination compressive strength, compressive modulus and/or dynamic modulus.

C. Using Aryl Glycolipid Gel Articles

An exemplary control-release application is in the honeybee industry. Bees are insects of the order Hymenoptera, and comprise a group of about 20,000 species throughout the world, known taxonomically as the Superfamily Apoidea. Honey bees of the genus *Apis* belong to the family Apidae, a sub-group of this superfamily. At least four species of honey bee are commonly recognized: the dwarf, or midget, bee *Apis florea*, the giant, or rock, bee *Apis dorsata*, the oriental (Indian, Chinese, Japanese, etc.) bee *Apis cerana*, and the common (European, African, etc.) honey bee *Apis mellifera*. The existence of another giant bee, *Apis laboriosa*, has recently been confirmed.

Honeybees, *Apis mellifera*, produce more than $270 million of honey and pollinate over $14 billion of crops annually in the U.S. alone. Thus, it is clear that maintaining healthy bee colonies is an essential aspect of much agricultural practice, and has significant economic impact.

Unfortunately, a serious worldwide threat to honeybees is the parasitic mite, Varroa destructor. Varroa mites can deform developing bees, cause weight loss and premature death and transmit various viral diseases. Mite infestations can completely destroy infected honeybee colonies in as little as a few weeks when remedial measures are not taken. Indeed, parasitic mite and mite-related diseases have already caused the death of about 95 to 98 percent of the wild honey bee colonies in the United States, and have put commercial colonies at risk. Thus, the Varroa mite represents a great threat to beekeeping.

Thus, in one exemplary embodiment, the invention provides a device for control-release of 2-heptanone, in an amount effective for the control of varroa mites in the honeybee hive. In one exemplary embodiment, the device for control-release of a 2-heptanone is bio-degradeable. In another exemplary embodiment, 2-heptanone gels are used in a method for controlling Varroa mites in honey bee hives comprising placing a device for control-release of 2-heptanone in a honey bee hive.

D. Packaging of Aryl Glycolipid Gel Articles

Semi-rigid gel articles are packaged in any convenient form known in the art. Indeed any suitable packaging can be used e.g., packaging as disclosed in U.S. Pat. No. 7,160,604, U.S. Pat. No. 3,809,220, U.S. Pat. No. 4,120,400 and U.S. Pat. No. 6,523,691. Typically, the packaging for a semi-rigid gel article resists air transmission so as to preserve the moisture content of the semi-rigid gel article. In some exemplary embodiments, several semi-rigid gel articles are packaged together, thus, providing multiple applications per container. In other exemplary embodiments, the semi-rigid gel article is packaged individually.

The following examples are offered to illustrate, but not to limit the invention.

EXAMPLES

Materials and Methods for Examples 1-5

Materials

2-Heptanone (CAS registry No. 110-43-0) was purchased from the Sigma-Aldrich Co. (St. Louis, Mo.). Peach fruit film (100 μm thickness) processed from a 3:1 blend of peach puree:pectin (Origami Foods, Stockton, Calif.) was used as a vapor barrier film for making control-release devices. Beeswax was purchased locally (Protex, Berkeley, Ca).

Preparation of Aryl Glycolipid

The aryl glycolipid was synthesized according to methods reported earlier (John, G., et al. (2001) *Advanced Materials* 2001, 13, (10), 715-718, which is incorporated herein by reference). Briefly, glucoside mixtures were fractionated using Yamazen fraction collector FR-50N coupled with a gradient mixer GR-200, a variable-wavelength UV detector prep UV-10-V, and a flat minirecorder. The sample was applied to medium-pressure column chromatography on a Yamazen ODS column (100×2.6 cm, i.d.) packed with ODS (50 μm particle size). The mobile phase used was methanol-10% aqueous acetic acid (initially 88:12., and after the sample injection the gradient mixer changed to 90:10, v/v, methanol:10% aqueous at 8 mL/min. The fractions were collected and dried to constant weight under vacuum at room temperature. The compounds were isolated and analyzed by standard methods.

2-Heptanone Gels

Gels containing 2-heptanone were made by weighing the prescribed amount of aryl glycolipid in an empty glass vial (1.5 cm dia., 2.5 cm length) and pipetting the 2-heptanone to obtain 3%, 5%, or 7% of the glycolipid in 2-heptanone (w/w). The vial was capped and then partially submerged in a water bath (80° C.) using a clamp. The vial contents were swirled intermittently to facilitate dissolution. Once the aryl glycolipid had completely dissolved in the 2-heptanone, the temperature of the water bath was slowly lowered. The aryl glycolipid began crystallizing and forming a gel at approximately 70° C. and eventually formed a solid, semitransparent gel upon further cooling to 60° C. The vials were then removed from the water bath and cooled to room temperature.

Differential Scanning calorimetry

Thermograms of the cooling properties of the gels were obtained by differential scanning calorimetry (DSC). 2-Heptanone gels with 7% solids were made as previously described. After cooling to room temperature, approximately 25 mg of gel (1.30 to 1.78 solids) was loaded and sealed in a stainless steel DSC capsule (model 1536, Perkin Elmer, Waltham, Mass.). Samples were heated from 25° C. to 95° C. in a DSC (model 2910 TA Instruments, New Castle, Del.) and then cooled to room temperature at a rate of 5° C./min.

Microscopy

Gel formation was monitored through a flat-bottomed 25 ml glass vial containing 2-heptanone (2 ml) and gelling agent (3%, w/w). The gelling agent was dissolved in 2-heptanone by heating to 80° C. in a water bath. Crystallization and gel formation during cooling were documented using a digital camera (Retiga 2000R, Q-Imagining, Surrey, BC, Canada) mounted on a stereo light microscope (Leica Model MZ 16F, Leica GmBH, Wetzlar, Germany). Photographs were taken every 3 s starting at the moment the first crystal was observed.

Scanning electron microscopy was done by first preparing a 5% gel sample in a glass vial as previously described. The gel was removed from the glass vial and sliced into pieces (ca. 5 mm). The samples were immediately placed in the chamber of a critical point dryer (Tousimis Autosamdri 815, Tousimis, Rockville, Md.) and equilibrated in liquid carbon dioxide for several hours to displace the 2-heptanone with liquid $CO_2$. After several exchanges over a period of several hours the samples were critical point dried before sputter coating with gold-palladium in a Denton Desk II Sputter Coating Unit (Denton Vacuum, Inc., Moorestown, N.J.). The samples were viewed and photographed with a Hitachi 54700 field emission scanning electron microscope (Hitachi, Japan).

Mechanical Properties

The mechanical properties of the gels were determined using both a penetrometer test as well as rheometry. For penetrometer tests, gel samples containing 3%, 5%, and 7% glycolipid were prepared in glass vials as previously described. Gel thickness was approximately 30 mm. Penetrometer tests were performed without removing the gels from the vials so that measurements could be recorded on undisturbed sample. Penetrometer tests were performed by pressing a flat-faced cylindrical probe (8 mm dia.) into the gel sample to a depth of 3 mm at a rate of 5 mm/min using a universal testing machine (model 4500, Instron Corp., Canton, Mass.). A load cell (100 N) was used to detect compressive force. Peak force, modulus, and toughness were determined from force/deformation data. Five samples were tested for each of the glycolipid concentrations prepared.

Dynamic rheological tests were performed using a Peltier plate rheometer (TA Instruments, model AR2000, New Castle, Del.). Gel samples of 3%, 5%, and 7% were prepared in glass vials as previously described. The gel was scooped from the vials with a spatula and placed on a Peltier plate. A stainless steel parallel plate (60 mm) was lowered onto the sample. The sample thickness was held constant at 1 mm. Dynamic rheological tests were used to characterize the elastic modulus (G') and viscous modulus (G"). The elastic modulus is a measure of the solid-like response of the material, whereas the viscous modulus is a measure of the liquid-like response of the material. All dynamic measurements were obtained at a frequency of 1 rad/s and a strain of 2%. In addition, all experiments were performed within the linear viscoelastic region.

Biodegradation

The relative degradation rate of samples was determined using a respirometer (Micro-Oxymax System, Columbus Instruments, Columbus, Ohio). The respirometer $CO_2$ sensor was calibrated with a $CO_2$ standard gas (8,000 ppm). The carbon content of the samples (60.8%) was determined according to ASTM methods using a CHN elemental analyzer (Perkin Elmer 2400, Boston, Mass.). The analyzer was equipped with a thermoconductivity detector and was operated using helium gas. The combustion temperature was 975° C. and the reduction temperature was 680° C.

Commercial compost was purchased locally and adjusted to 58% moisture (dry weight basis). The glass sample bottles (250 ml) were filled with 20.0 g compost and 0.30 g test sample that was gently mixed with the compost. The sample bottles were initially flushed with $CO_2$-free air and sealed. Respirometry experiments were conducted at room temperature (22° C.) and $CO_2$ concentration was read every 12 hr. Three replications were tested for each treatment and data were expressed in terms of percentage mineralization.

Evaporation Rate

The relative rate of evaporation between liquid 2-heptanone and a 2-heptanone gel was determined by monitoring weight loss of both materials under the same conditions. The tests were performed using aluminum sample dishes (50 mm dia., 20 mm depth). The dishes were filled (5 g) with 2-heptanone liquid (control) or gel (treatment). The gel was formed by heating (80° C.) a glass vial containing 2-heptanone and 7% aryl glycolipid. The heated contents (5 g) were poured into an aluminum sample dish and immediately covered to minimize evaporation. The samples were allowed to equilibrate 1 hr at room temperature. All samples were uncovered and placed in a poly(methyl methacrylate) cabinet equipped with a ventilation fan. The airflow velocity was 9.8 m/s, and the airflow volume was 4.7 volume changes per second (9.9 m$^3$/min). All tests were performed at room temperature. The samples were weighed regularly to monitor weight loss.

Controlled-Release

Control-release devices made with the 2-heptanone gel were compared with a standard control-release device made with beeswax as a reservoir material. The beeswax devices were made by first preparing the reservoir material. This was accomplished by dissolving beeswax in 2-heptanone (1:1) in a sealed glass jar at elevated temperatures (80° C.). The molten mixture was poured into a disk mold (3 mm thick, 10 cm diameter) and allowed to cool and solidify. Specimens weighing 3.2 g were cut from the beeswax/2-heptanone disc and sealed within a vapor barrier film envelope using a heat sealer (Model 2526, Clamco, Cleveland, Ohio) operated at 405° C. The 2-heptanone gel samples were made by preparing a 3% (w/w) aryl glycolipid in 2-heptanone in a sealed glass vial. The mixture was heated to 80° C. in a water bath and samples weighing 3.2-3.5 g were poured into a film envelope and sealed closed as previously described.

All control-release experiments were performed in duplicate. Loss of 2-heptanone from the devices was measured as weight loss. To activate release of 2-heptanone, an 8 mm hole was made in the film envelope of each sample. Experiments were run until 50% or more of the 2-heptanone had been lost.

Example 1

Preparation of Aryl-Glycolipid Gels

The following Example illustrates making of solid reversible gels with 2-heptanone and aryl glycolipid.

Solid, reversible gels were made with 2-heptanone and the aryl glycolipid. One exemplary value of having a gel as a matrix for the reservoir of a control-release device is that it prevents the 2-heptanone liquid from leaking out of the reservoir should a break or tear in the vapor barrier film occur. In some gels, a certain amount of liquid may separate due to syneresis. Syneresis could facilitate leakage from the reservoir should a tear or pin hole develop in the vapor barrier film. Some syneresis was observed in gels containing 3% aryl glycolipid. However, there was little or no syneresis observed in the sample containing 5% and 7% aryl glycolipid. As a result, aryl glycolipid concentrations of 5% or greater should be used in control-release devices to minimize syneresis.

Figure 1:
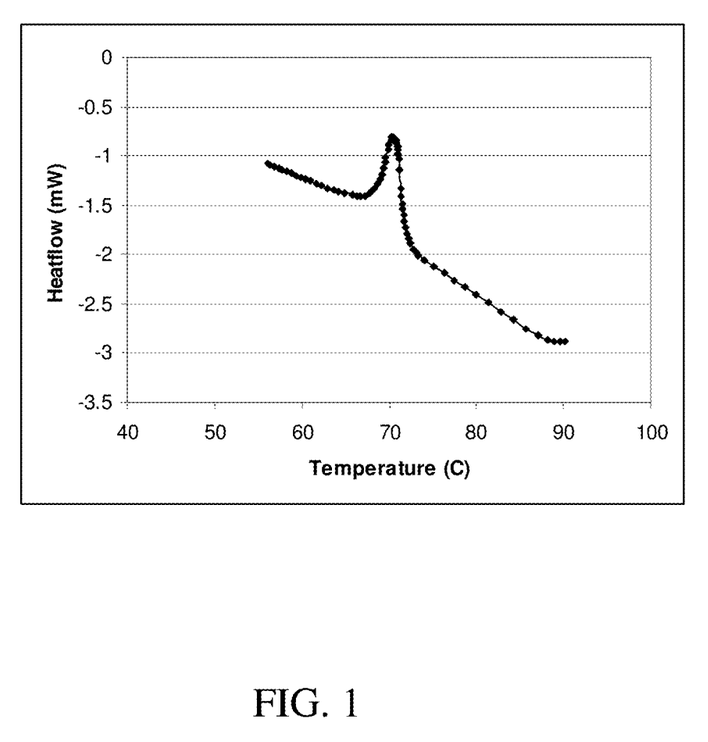
FIG. 1. DSC curves of 2-heptanone containing an aryl glycolipid (7% w,w) during cooling. The cooling rate was 5° C./min.

The thermal properties of the gels upon cooling from 90° C. were monitored by DSC. An exotherm was observed at 70° C. which corresponded with the crystallization/gelation of the mixture (FIG. 1). The crystallization temperature (71) varied from sample to sample by as much as 8° C. Among other factors, $T_c$ of materials during cooling may be affected by variables such as cooling rate and polymer chain length (18-20).

Example 2

Microscopy

The following Example illustrates light microscopy for documenting the gelling behavior of the aryl glycolipid/2-heptanone mixture.

Figure 2:
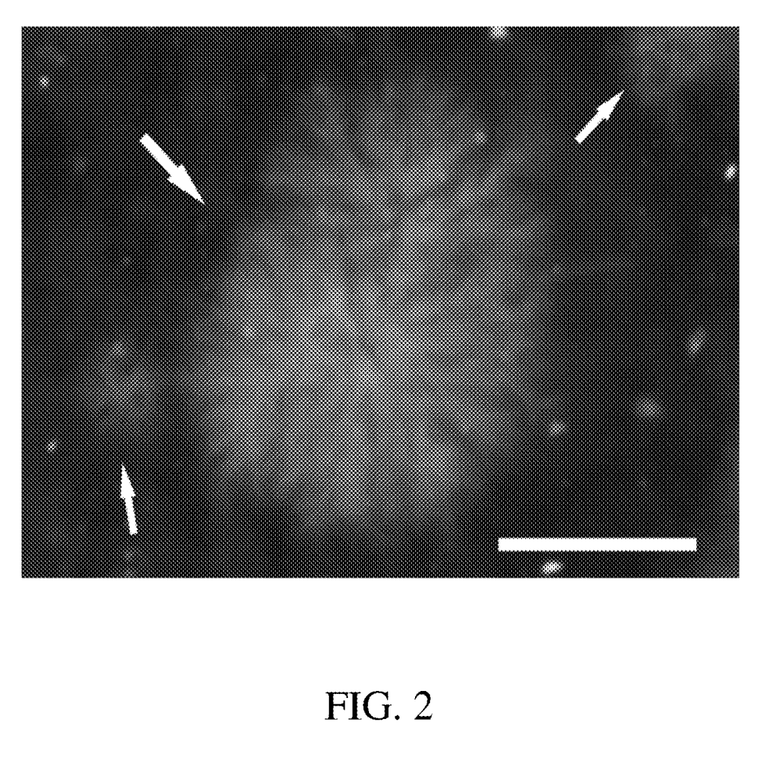
FIG. 2. Micrograph of crystals forming in aryl glycolipid/2-heptanone mixture. Note the presence of crystals at various stages of growth (see arrows). Random nucleation of crystals was followed by rapid crystal growth and gelation. (Scale bar=400 µm)
Figure 3:
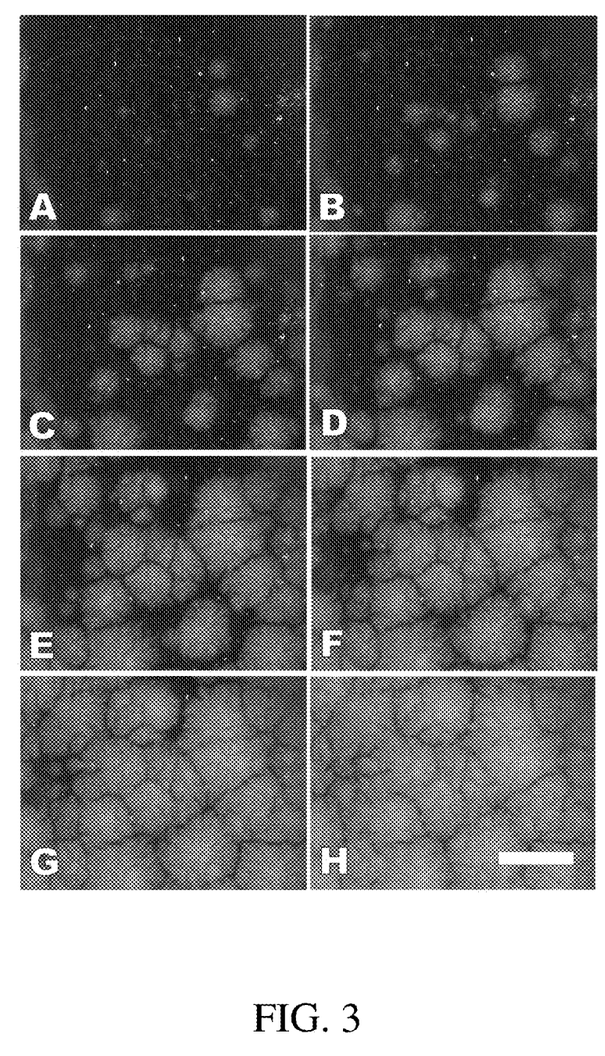
FIG. 3. Micrographs of sequential views during the gelling process of the aryl glucolipids in 2-heptanone. Scale bar=1 mm.

Light microscopy was effective in documenting the gelling behavior of the aryl glycolipid/2-heptanone mixture (FIG. 2). Samples that were heated to 80° C. and cooled typically demonstrated the appearance of small crystals as the $T_c$ was approached (FIG. 3A). The crystals quickly grew and new crystals formed randomly throughout the mixture upon further cooling. Sequential micrographs of the crystals revealed that the crystals typically grew until they reached adjacent crystals (FIGS. 3A-H). Individual crystals initially remained distinct as the void spaces were filled. With time, however, it became more difficult to distinguish individual crystals as the gel solidified (FIG. 3H). Crystal diameters were as large as 1 mm (FIG. 3H).

Figure 4:
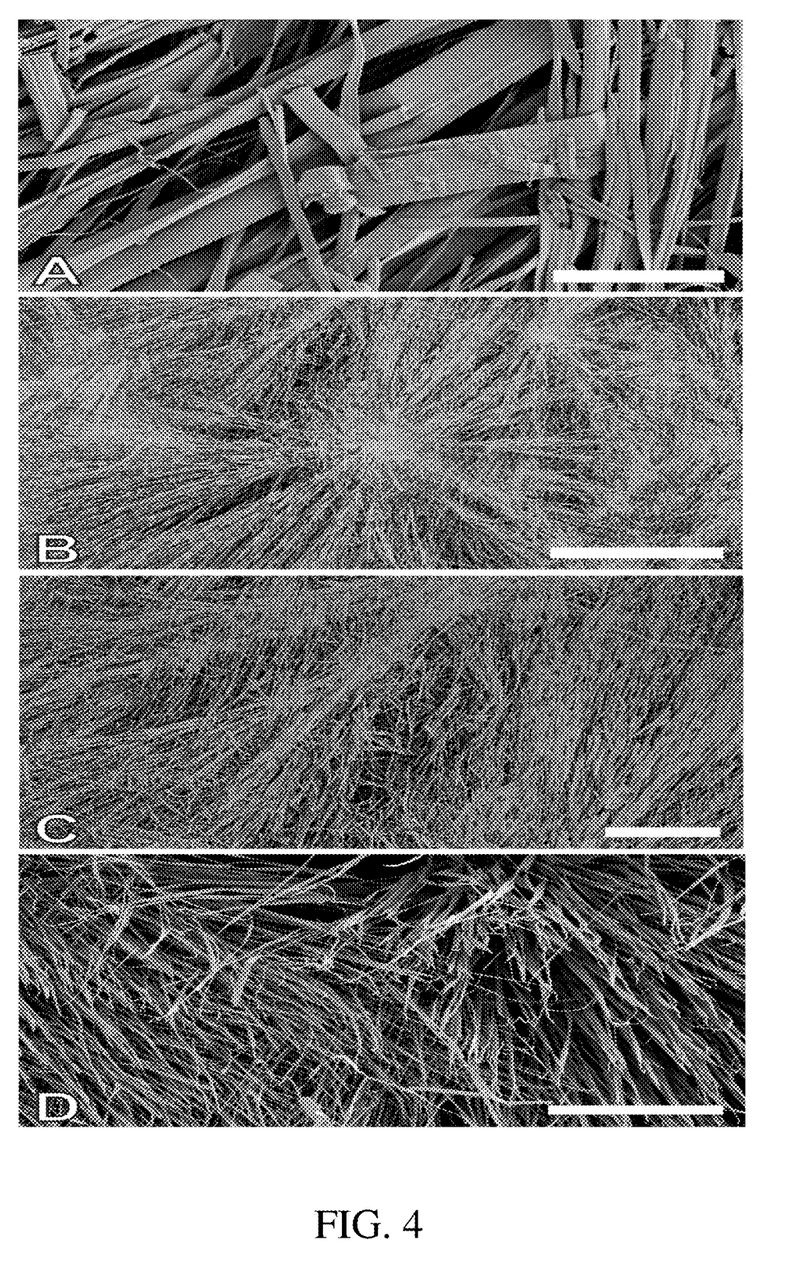
FIG. 4. Scanning electron micrograph of aryl glycolipid comprising the gel matrix. Scale bar A=10 µm; scale bar B=300 µm; scale bar C=100 µm; scale bar D=30

Samples that were critical point dried using $CO_2$ in preparation for SEM were very well preserved (FIG. 4). The 2-heptanone was miscible with the liquid $CO_2$ and was freely exchanged during the purging steps. Micrographs (SEM) of cross-sectional views revealed that the star-shaped crystals observed by light microscopy were comprised of thin fibers emanating from the nucleating site (FIGS. 4A-B). The fibers were generally oriented in the direction of crystal growth which was outward from the core nucleation site (FIG. 4C). Fibers at the outer edge of the crystals contained the terminal points and were generally of much smaller thickness compared to fibers near the nucleation site (FIG. 4D). The fiber density was greatest near the region where crystal nucleation occurred (FIG. 4B). The fiber orientation was less apparent in regions where the terminal ends of adjacent fibers intersected and intertwined. Such intertwining of adjacent crystals most likely contributed to the over strength and rigidity of the gel structure.

Example 3

Mechanical Properties

The following Example illustrates mechanical properties of gels prepared from the aryl glycolipid/2-heptanone mixture.

Figure 5:
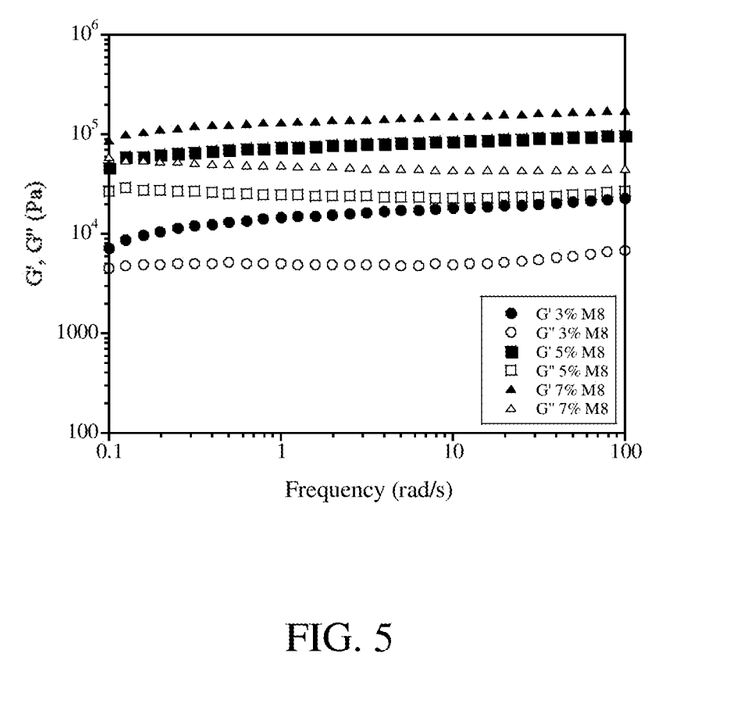
FIG. 5. Dynamic rheological properties of three different gels containing 3%, 5%, and 7% of aryl glycolipid (M8). Elastic modulus (G') and viscous modulus (G") for each concentration of glycolipid were determined as a function of frequency.
Figure 6:
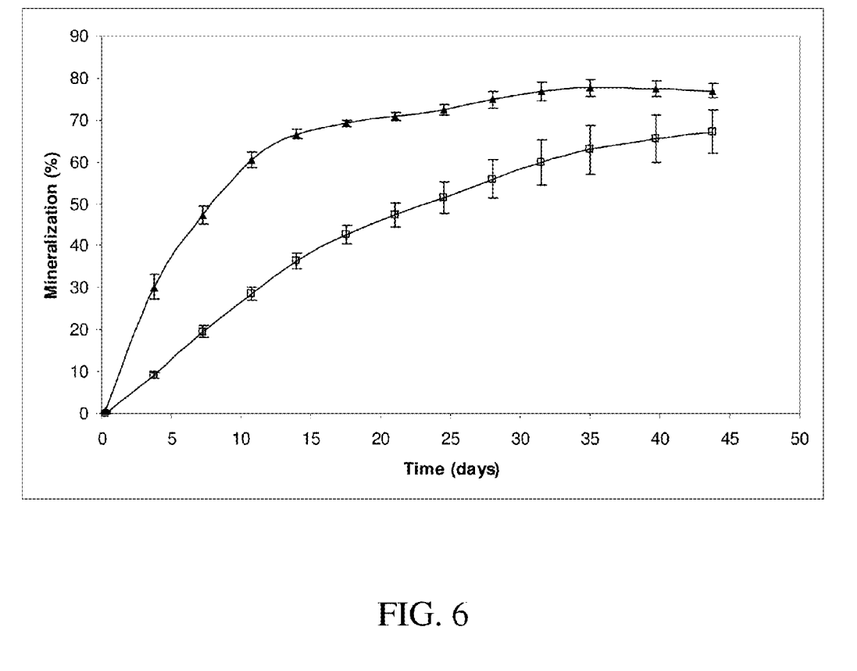
FIG. 6. Percent mineralization of aryl glycolipid (□) and starch control (▲) over time (days). Error bars represent standard deviation.
Figure 7:
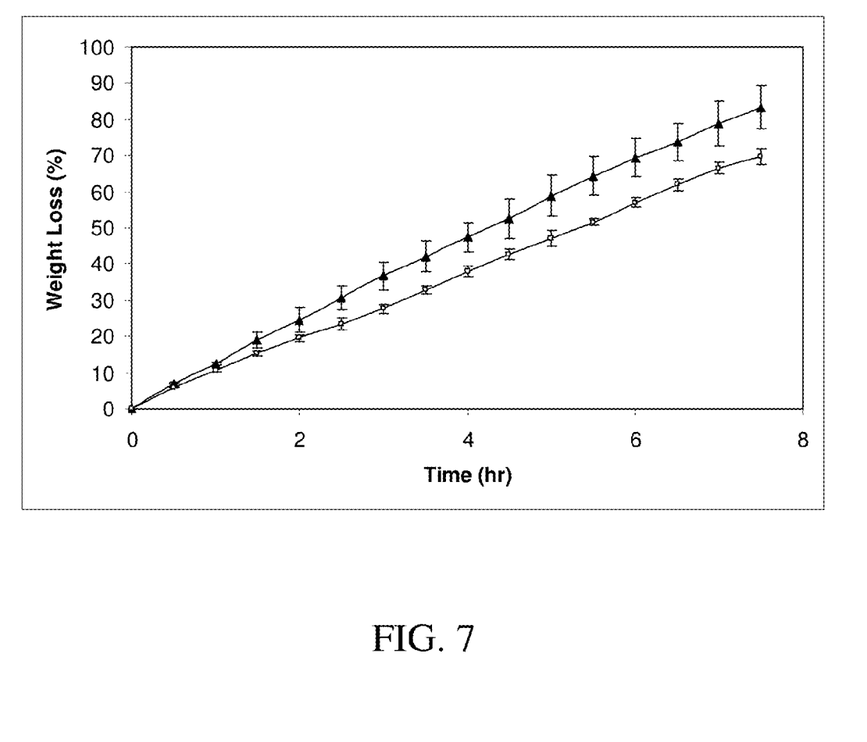
FIG. 7. Weight loss from evaporation of 2-heptanone from a liquid (O) or 2-heptanone gel (▲).
Figure 8:
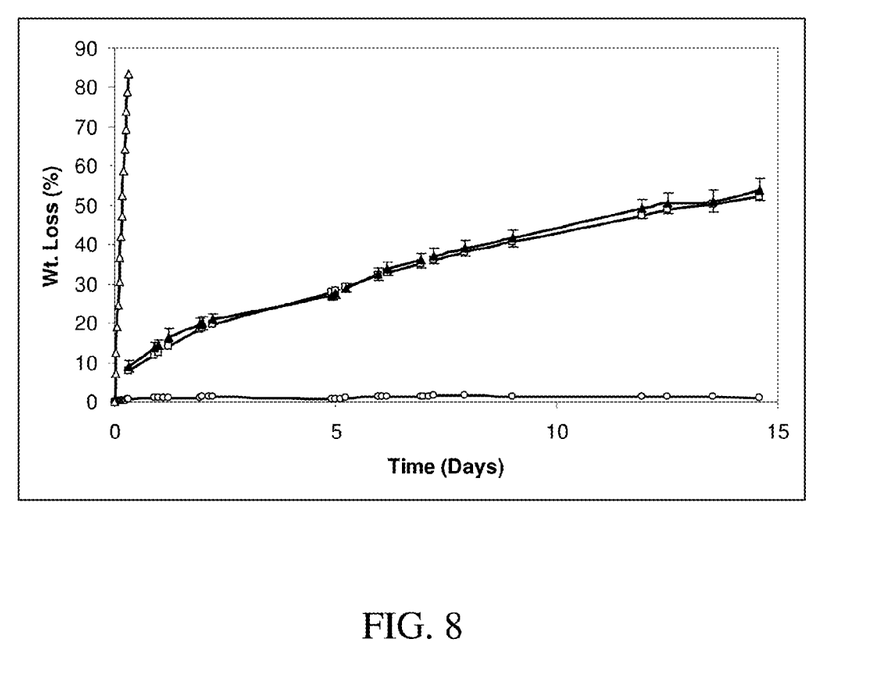
FIG. 8. Percent weight loss over time of two controls and two activated control-release devices. Controls consisted of a gel without a vapor barrier (Δ) and a gel completely sealed in a vapor barrier film (O). Activated control-release devices were sealed in a vapor barrier film that contained a small opening. The devices contained either a 2-heptanone gel (□) or a blend of beeswax and 2-heptanone (▲). Error bars (standard deviation) are for the control release device containing beeswax FIG. 9. Weight loss over time of control-release devices. The control (O), which was sealed in vapor barrier film, had very little weight loss during the time period tested. The device containing 2-heptanone gel (□) had double the weight loss compared to the devices containing beeswax (▲).
Figure 9:
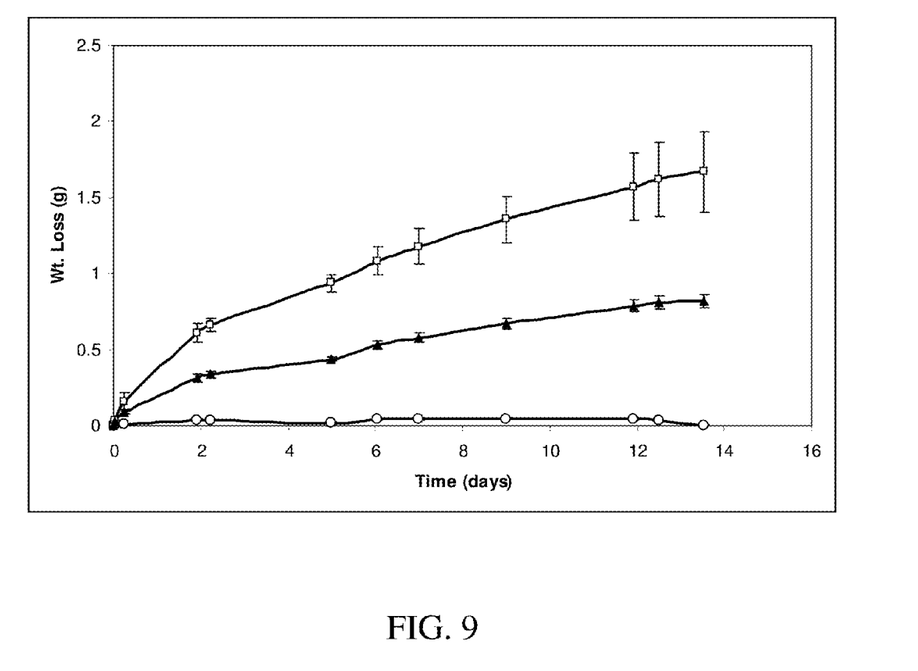

The dynamic rheological properties of three different gels containing 3%, 5%, and 7% aryl glycolipid were examined (FIG. 5). All samples had G' (elastic modulus) values greater than G" (viscous modulus) values, indicating each sample exhibited more solid-like than liquid-like behavior. For the 3% aryl glycolipid sample, the G' values were mostly independent of frequency, but did show some dependence at lower frequencies. This result suggested that the sample was a soft gel. For the 5% and 7% aryl glycolipid samples, the G' values were less dependent on frequency than the 3% sample, indicating more well developed gels. In addition, samples containing higher concentrations of aryl glycolipid had greater G' values, which also indicated the presence of stronger gels.

The behavior of the 2-heptanone gels under compressive stress was of interest since control-release devices may be subjected to compressive stress during shipment or when placed in honeybee colonies. Compression tests indicated that strength, modulus, and toughness of 2-heptanone gels increased with increasing concentrations of the aryl glycolipid (Table 1).

TABLE 1

Compressive strength, modulus, and toughness of 2-heptanone gels containing 3%, 5%, and 7% aryl glycolipid.

| Gel Concentration | Compressive Strength (kPa) | Modulus (kPa) | Toughness (kPa) |
|---|---|---|---|
| 3% | 1.3 (± 0.26) | 6.8 (± 4.1) | 0.77 (± 0.17) |
| 5% | 4.0 (± 0.13) | 13.5 (± 6.8) | 2.4 (± 0.77) |
| 7% | 7.5 (± 2.5) | 23.6 (± 8.1) | 4.7 (± 1.3) |

As previously mentioned, gels containing 3% aryl glycolipid exhibited some syneresis. However, compressive stress induced further syneresis in the 3% and also in 5% aryl glycolipid gels. However, little or no stress-induced syneresis was observed in gels containing 7% aryl glycolipid.

Example 4

Microscopy

The following Example illustrates biodegradation characteristics of the aryl glycolipid/2-heptanone mixture.

The degradation properties of materials used in control-release devices are important because labor costs can be minimized if spent devices can be left in the field to degrade naturally. Starch is a common food commodity and is one of the most readily degradable polymers in nature. The mineralization rate of the aryl glycolipid was compared to that of a starch control (FIG. 6). The aryl glycolipid mineralized at nearly the same rate as the starch control (FIG. 6). In an exemplary embodiment, aryl glycolipids are used in agricultural control-release devices could provide important functionality and environmental compatibility.

Example 5

Controlled Release

The following Example illustrates controlled release properties of gels prepared from the aryl glycolipid/2-heptanone mixture.

Evaporation rates for gels versus 2-heptanone liquid were measured to determine whether the gel structure itself would affect the rate of 2-heptanone loss. The data indicate the gel structure does not reduce the evaporation rate of 2-heptanone and may have slightly increased it (FIG. 7). The rate of 2-heptanone loss was markedly reduced by sealing the 2-heptanone gel in a vapor barrier film (FIG. 8). There was little change in weight observed in gel samples completely sealed within the vapor barrier film. Samples activated by boring a small hole in the vapor barrier slowly released 2-heptanone over time (FIG. 8). The percent weight loss of the samples over time was very similar for samples containing either a 2-heptanone gel or a 50:50 blend of beeswax and 2-heptanone. However, the device containing the 2-heptanone gel could load approximately twice the amount of 2-heptanone compared to the device with beeswax. As a result, for control-release devices of a given weight the gel-containing device delivers approximately twice the amount of active agent as the control (FIG. 9). The results support the value of aryl glycolipids in gelling 2-heptanone for use in reservoir-type, biodegradable control-release devices.

Thus, in an exemplary embodiment, a device for control-release of a volatile liquid comprises a barrier layer which at least partially surrounds the 2-heptanone gel.

In one exemplary embodiment, a carbohydrate-based material is used as a vapor barrier. In an exemplary embodiment, the barrier layer is a fruit film. Any fruit can be used to form the film. In one exemplary embodiment, the fruit film comprises peach puree. In one exemplary embodiment, the fruit film comprises apple puree. In one exemplary embodiment, the fruit film comprises pear puree. Methods for producing fruit films and formed food products from dehydrated fruits and vegetables are known in the art see e.g., U.S. Pat. No. 6,623,779 and U.S. Pat. No. 6,027,758 each of which is incorporated herein by reference.

In other exemplary embodiments the film layer comprises vegetables. In one exemplary embodiment, the fruit film comprises tomato puree. In another exemplary embodiment, the fruit film comprises broccoli puree. In another exemplary embodiment, the fruit film comprises pea puree.

In another exemplary embodiment, the barrier layer is a fruit film, and the barrier layer is at least partially surrounded with an outer coating layer. In an exemplary embodiment, beeswax is an outer coating layer. An outer coating layer may be applied by any method known in the art e.g., by dipping the control-release device comprising a 2-heptanone gel at least partially surrounded by a barrier layer in a substance effective as an outer coating layer e.g., beeswax. Thus in an exemplary embodiment, the device for controlled release of a volatile chemical is effective to control parasitic mites e.g., Varroa destructor, in honey bee hives.

The fruit and/or vegetable film can be applied by any method known in the art. For example in an exemplary embodiment, the film is wrapped around the 2-heptanone gel to provide a barrier layer. In another exemplary embodiment, the film is applied by dipping the 2-heptanone gel in a solution comprising fruit and/or vegetable puree and allowing the puree to cure to a film around the 2-heptanone gel thus providing a barrier layer.

Example 6

Controlled Release Device for Honey Bee Hives

The following Example illustrates the use of aryl glycolipid gels as a controlled release device for delivery of pheromones to honey bee hives.

Mannitol dioctanoate (M8, see FIG. 10) was used to gel the pheromone 2-heptanone and thus prepare a controlled release device (CRD) for use in honey bee hives.

2-Heptanone is a natural compound produced by honey bees that enables them to dissolve plant waxes as well as beeswax. At elevated levels, it controls parasitic mites, varroa (Varroa destructor), that infest and destroy honey bee colonies in a short period of time.10 In order to effectively control mites, the miticide (2-heptanone) needs to last at least 2 brood cycles or 42 days. However, due to the high vapor pressure (0.48 kPa at 20 C) and elevated temperatures existing in bee hives (average 30 C), 11 the 2-heptanone volatilizes at a faster rate.

2-Heptanone gels were made with M8 at different concentrations (3, 5 and 7% wt/v) as discussed in Materials and Methods for Examples 1-5. The gels were characterized for mechanical, syneresis and thermal properties, as discussed above in Examples 1-5. Dynamic rheological measurements were performed within a linear viscosity regime to determine the mechanical strength of gels. From the frequency sweep experiments, the $G^0$ and $G^{00}$ were found to be independent of oscillatory frequency, except at lower values, where very weak dependency was observed. The $G^0$ (elastic modulus) values were considerably higher than $G^{00}$ (viscous modulus)

values, regardless of concentration. All the gels exhibited moderate elastic behavior and did not relax over the entire experimental time. For 5 and 7% wt/v gels, average $G^0$ values were found to be greater than that of 3% by an order of magnitude (Table 2). Thus, $G^0$ being a measure of the solid nature of a gel, 3% gel is categorized as soft gel, compared to well developed and stronger gels of higher concentrations (5 and 7%).

TABLE 2

Thermal and mechanical properties of 2-heptanone gels of M8

| | 2-Heptanone gel concentration (% wt/v of M8) | | |
|---|---|---|---|
| | 3 | 5 | 7 |
| $T_g$/° C. | 62-64 | 65-68 | 70-72 |
| $G'$/kPa | 14.64 | 73.85 | 131.7 |
| Modulus/kPa | 6.8 (+/− 4.1) | 13.5 (+/− 6.8) | 23.6 (+/− 8.1) |
| Toughness/kPa | 0.77 (+/− 0.17) | 2.4 (+/− 0.77) | 4.7 (+/− 1.3) |
| $CS^a$/kPa | 1.3 (+/− 0.26) | 4.0 (+/− 0.13) | 7.5 (+/− 2.5) |

$^a$CS ¼ compressive strength

Compression tests indicated that the strength, modulus, and toughness of 2-heptanone gels increased with increasing concentrations of M8 (Table 2). Compressive stress-induced syneresis was observed in a 3% gel, whereas a 5 or 7% gel had little or no stress-induced syneresis. Thermal stability, or the gel-to-sol transition temperature (Tg), was determined by the table-top tube inversion method as known in the art (see e.g., F. M. Menger and K. L. Caran, J. Am. Chem. Soc., 2000, 122, 11679). As expected, the Tg was proportional to the concentration of M8 (Table 2). Tg values were greater than the average bee colony temperature, where the highest Tg value was 70 C for a 7% gel. Initial gel characterization results suggested that gels with an M8 concentration of 5% or greater have strong potential as components of CRDs.

Morphology and molecular aggregation were studied using various techniques to elucidate the gelation mechanism (see e.g., FIG. 3. and FIG. 4). Optical microscopy analyses of 2-heptanone gel (5% wt/v) showed uniformly distributed clusters of spherulite-like crystals (see e.g., FIG. 3 Further details on morphology were acquired by using a high resolution field emission scanning electron microscope (SEM). Gels were critical point dried from liquid CO2 before making samples for SEM.13 The morphology of the dried sample was in good concordance with that observed in the wet condition under the optical microscopy, indicating that critical point drying preserved the native structure of the gel. Micrographs revealed the star-shaped crystals comprised of ribbons radiating out from the core nucleation site (see e.g., FIGS. 4B and 4C). The ribbon density was greatest near the region where nucleation occurred. The terminal points of ribbons were thinner than those near the nucleation site (see e.g., FIG. 4D). The orientation of ribbon was less apparent in regions where the terminal ends of adjacent crystals intersected. Such intertwining resulted in the formation of crystal clusters, which most likely contributed to the overall strength and rigidity of the gel structure.

To elucidate possible molecular aggregation, X-ray diffraction (XRD) was performed on xero- and native gels of M8 in 2-heptanone and compared to the M8 powder. M8 exhibited similar XRD patterns in both xerogel and powder state, i.e. it self-assembles in a similar manner in the gel and the solid state. Based on Bragg spacing ratio (1:½:⅓:¼), the self-assembly mode for M8 was postulated to follow well-ordered lamellar stacking (see e.g., L. A. Estroff and A. D. Hamilton, Chem. Rev., 2004, 104, 1201 The probable ordered structure was modeled by using an energy-minimized M8 molecule and correlating its size to the d-spacing of the native gel (2.82 nm). The multilayer molecular stacking is stabilized by extensive hydrogen bonding between the sugar groups and van der Waals interaction between alkyl chains, as confirmed by IR spectroscopy.

Before using the M8-based gels for CRDs the 2-heptanone gels of M8 were further analyzed to determine their suitability for use in apiculture. Specifically they were analysed to determine if the CRDs were: (i) biocompatible with the beneficial organism (bees in present case), so that they do not disrupt their normal behavior, and (ii) naturally biodegradable, to preclude the need and associated cost to recover spent devices.15 The use of biobased precursors, mannitol and caprylic acid, ensures that the gelators are safe and biodegradable. Biodegradability of M8 was computed in terms of mineralization rate and was compared to that of a starch control.

Starch is a common food commodity and is one of the most readily degradable polymers in nature. As depicted in FIG. 6, M8 is a readily biodegradable material, since it mineralized at nearly the same rate as the starch control. Thus, the use of sugar-gelators, such as M8, inagricultural controlled release devices thus provides functionality and environmental compatibility.

To determine the efficacy of the gel matrix per se in controlling the release of pheromone, the relative rate of evaporation between liquid 2-heptanone and a 2-heptanone gel (7% wt/v) was investigated by monitoring weight loss of both materials under the same conditions.

The data indicate that 2-heptanone volatilized as quickly from the gel as it did from liquid 2-heptanone. The inefficiency in controlling the release can be attributed to the clustered aggregation of the self-assembled structure. Clusters are known to be less effective in entrapping organic liquids than the long entangled fibers (see e.g., A. Vallet, P. Cassier and Y. Lensky, J. Insect Physiol., 1991, 37, 789).

However, the ability of M8 to immobilize pheromones at low concentration (#7% wt/v) without exhibiting any syneresis on application of high compressive stress ensures a high loading-capacity and leak-free performance which, in turn, enhance its utilization in developing a reservoir type CRD.

Finally, a reservoir-type CRD was developed by using M8. Like previously developed CRDs, the current device consisted of a reservoir of a 2-heptanone gel (7% wt/v) sealed in a pouch made from a semi-permeable membrane (vapor barrier film). The membrane is a fruit film made entirely of agricultural materials and is easily heat sealable, which facilitates encasing the reservoir (see e.g., G. M. Glenn, et al. Agric. Food Chem., 2006, 54, 3297, which is incorporated herein by reference). The rate of 2-heptanone loss was markedly reduced by sealing the 2-heptanone gel in a vapor barrier film (FIG. 5). Very little change in weight was observed in a completely sealed CRD. However, samples activated by boring a small hole in the vapor barrier slowly released 2-heptanone over time (as seen e.g., in FIG. 8). The gel-based CRD was compared to a standard controlled release device made with beeswax as the reservoir material. The percent weight loss of the gel-based CRDs was similar to the CRD consisting of 1:1 blends of beeswax and 2-heptanone.

Advantageously, the loading capacity of the gel-based device (92% wt/wt) was approximately two-fold greater than that of the beeswax containing device (50% wt/wt). As a result, for controlled release devices of a given weight, the gel-containing device delivers approximately twice the amount of active ingredient as the control device. The results suggest that the M8 immobilizes the 2-heptanone in the reservoir and provides a means of loading a very high concentration of 2-heptanone into the reservoir. The high concentration loading capacity will allow for smaller devices with equal or higher delivering capacity than other devices. In addition, the high solid content in CRDs made with other reservoir materials will reduce the degradation rate of devices. The degrading material may attract unwanted pests and cause problems. On the contrary, owing to minimal solid content and high biodegradability of gelators, gel-based CRDs, once spent, will degrade rapidly, thereby minimizing the unwanted pest attraction problem.

In conclusion, the application of molecular gels in the agricultural industry was demonstrated by utilizing efficient pheromone-gelling sugar gelators, such as M8, to develop reservoir-type CRDs. The use of a biobased gelator ensures higher biocompatibility and biodegradability of devices. Thus, CRDs with high loading capacity and the delivery of pheromone at high concentration were developed. The efficiency of gels pertaining to targeted application depends on various factors, for example gel-solvent interactions, gel morphology, etc., which will be explored in future development of effective molecular gel-based CRDs It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A controlled release device (CRD) comprising:
a solid gel of a pheromone, and an impermeable membrane at least partially surrounding the solid gel of pheromone,
wherein
the solid gel of pheromone comprises mannitol dioctanoate (M8) at a concentration that is in a range of between about 0.5% weight/weight (w/w) to about 10% w/w.

2. The CRD of claim 1, wherein the pheromone is soluble or insoluble in water.

3. The CRD of claim 1, wherein the pheromone is a member selected from the group consisting of 2-heptanone, laurel acetate, 1-Octen-3-ol, Z-3-Decenyl Acetate, 6-acetoxy-5-Hexadecanolide, Z-7-Decenyl Acetate, cis-5-Decenyl acetate, e,e-8,10-DODECADIEN-1-YL ACETATE, 8,10-Dodecadien-1-ol, z-5-DODECEN-1-YL ACETATE, e-7-Dodecen-1-yl acetate, E-beta-farnesene, Cyclobutaneethanol, 1-methyl-2-(1-methylethenyl)-, cis-3,3-Dimethyl-D1,b-cyclohexaneethanol, (Z)-3,3-Dimethyl-D1,acyclohexaneacetaldehyde, cis-6-Heneicosen-11-one, (cis-7,cis-11/cis-7,trans-11)-Hexadecadienyl acetate, 2-heptanone and 4-Methyl-5-Nonanone.

4. The CRD of claim 3, wherein the pheromone is 2-heptanone.

5. The CRD of claim 4, wherein controlled release device is placed in a honey bee hive and thereby, is used to control Varroa mites in honey bee hives.

6. The CRD of claim 1, wherein the mannitol dioctanoate (M8) is present at a concentration in a range of between about 3% weight/weight (w/w) to about 10% w/w.

7. The CRD of claim 6, wherein the mannitol dioctanoate (M8) is present at a concentration in a range of between about 5% weight/weight (w/w) to about 7% w/w.

8. The controlled release device of claim 1, wherein the impermeable membrane is a member selected from the group consisting of a fruit film, a poly(vinyl alcohol) (PVA) film, a ethylene (vinyl alcohol) (EVA) film and a cellulose film.

9. A controlled release device (CRD) comprising a solid gel of 2-heptanone, and an impermeable film at least partially surrounding the solid gel of 2-heptanone, wherein the solid gel of 2-heptanone comprises mannitol dioctanoate (M8) at a concentration that is in a range of between about 5% weight/weight (w/w) to about 7% w/w.

10. The CRD of claim 9, wherein the impermeable film is a member selected from the group consisting of a fruit film, a poly(vinyl alcohol) (PVA) film, a ethylene (vinyl alcohol) (EVA) film and a cellulose film.

11. The CRD of claim 9, wherein the controlled release device is placed in a honey bee hive and thereby, is used to control Varroa mites in honey bee hives.

12. A method for controlling Varroa mites in honey bee hives, the method comprising:
placing a controlled release device (CRD) into a honey bee hive,
wherein
the controlled release device comprises a solid gel of 2-heptanone, and an impermeable film at least partially surrounding the solid gel of 2-heptanone
wherein
the solid gel of 2-heptanone comprises mannitol dioctanoate (M8) at a concentration that is in a range of between about 5% weight/weight (w/w) to about 7% w/w.

13. The CRD of claim 10, wherein the impermeable film is a fruit film, and wherein the fruit film is at least partially surrounded by an outer coating layer that consists essentially of beeswax.

14. The CRD of claim 13, wherein the controlled release device is placed in a honey bee hive and thereby, is used to control Varroa mites in honey bee hives.

* * * * *